(12) United States Patent
Yun

(10) Patent No.: US 6,582,433 B2
(45) Date of Patent: Jun. 24, 2003

(54) SPINE FIXATION DEVICE AND METHOD

(75) Inventor: David Yun, Norden, CA (US)

(73) Assignee: St. Francis Medical Technologies, Inc., Concord, CA (US)

(*) Notice: Subject to any disclaimer, the term of this patent is extended or adjusted under 35 U.S.C. 154(b) by 0 days.

(21) Appl. No.: 09/829,321

(22) Filed: Apr. 9, 2001

(65) Prior Publication Data

US 2002/0147449 A1 Oct. 10, 2002

(51) Int. Cl.[7] .............................................. A61B 17/70
(52) U.S. Cl. ............................................................ 606/61
(58) Field of Search ........................ 606/61; 623/17.11, 623/17.12–17.16

(56) References Cited

U.S. PATENT DOCUMENTS

| | | |
|---|---|---|
| 2,677,369 A | 5/1954 | Knowles |
| 3,426,364 A | 2/1969 | Lumb |
| 3,648,691 A | 3/1972 | Lumb et al. |
| 3,867,728 A | 2/1975 | Stubstad et al. |
| 3,875,595 A | 4/1975 | Froning |
| 4,309,777 A | 1/1982 | Patil |
| 4,349,921 A | 9/1982 | Kuntz |
| 4,369,769 A | 1/1983 | Edwards |
| 4,401,112 A | 8/1983 | Rezaian |

(List continued on next page.)

FOREIGN PATENT DOCUMENTS

| | | |
|---|---|---|
| CA | 2015507 | 1/1991 |
| DE | 2821678 A1 | 4/1980 |
| DE | 3113142 A1 | 1/1982 |
| EP | 140790 A2 | 10/1984 |
| EP | 146347 A1 | 12/1984 |
| EP | 0677277 A2 | 10/1995 |
| EP | 0767636 B1 | 4/1997 |
| EP | 1138268 | 4/2001 |
| FR | 322334 A | 9/1989 |

(List continued on next page.)

OTHER PUBLICATIONS

Minns, R.J., et al., *Preliminary Design and Experimental Studies of a Novel Soft Implant for Correcting Sagittal Plane Instability in the Lumbar Spine*, SPINE vol. 22, No. 16, pp. 1819–1825, © 1997, Lippincott–Raven Publishers.

Waldemar Link, brochure entitled *Wirbelsäulen–Chirurgie: Instrumentarium Und Implantate Zur Wirbelsäulen–Chirurgie* (Spinal Surgery: Instrumentation and Implants for Spinal Surgery), Waldermar Link, Hamburg, Germany.

Haruo Tsuji, et al., *Ceramic Interspinous Block (CISB) Assisted Anterior Interbody Fusion*, Journal of Spinal Disorders, vol. 3, No. 1, pp. 77–86, ©1990 Raven Press, Ltd., New York.

Richard W. Porter, MD, FRCS, FRCSE, *Spinal Stenosis and Neurogenic Claudication*, SPINE vol. 21, No. 17, pp. 2046–2052, ©1996, Lippincott–Raven Publishers.

*Primary Examiner*—Kevin Shaver
*Assistant Examiner*—Michael B. Priddy
(74) *Attorney, Agent, or Firm*—Fliesler Dubb Meyer & Lovejoy LLP

(57) ABSTRACT

The present invention is a device and method that immobilizes the vertebral bodies by immobilizing the respective spinous process extending therefrom. The device contains a spacer extending from a body with the spacer adapted to be positioned between adjacent spinous processes so that the spacer may be located close to the spine. A strap connected with the body is designed to engage the spinous processes, such that the device may be adjusted to be positioned about the spinous processes. The device ensures that the spacer remains positioned between adjacent spinous processes. The method to insert the device minimizes destruction to body tissue, thus it is less traumatic to the patient and allows for the patient to recover from the procedure faster than conventional methods.

52 Claims, 5 Drawing Sheets

U.S. PATENT DOCUMENTS

| | | | |
|---|---|---|---|
| 4,479,491 A | 10/1984 | Martin | |
| 4,501,269 A | 2/1985 | Bagby | |
| 4,553,273 A | 11/1985 | Wu | |
| 4,554,914 A | 11/1985 | Kapp et al. | |
| 4,599,084 A | 7/1986 | Nashef | |
| 4,599,086 A | 7/1986 | Doty | |
| 4,604,995 A | 8/1986 | Stephens et al. | |
| 4,611,582 A | 9/1986 | Duff | |
| 4,636,217 A | 1/1987 | Ogilvie et al. | |
| 4,643,178 A | 2/1987 | Nastari et al. | |
| 4,657,550 A | 4/1987 | Daher | |
| 4,685,447 A | 8/1987 | Iversen et al. | |
| 4,696,290 A | 9/1987 | Steffee | |
| 4,714,469 A | 12/1987 | Kenna | |
| 4,743,256 A | 5/1988 | Brantigan | |
| 4,772,287 A | 9/1988 | Ray et al. | |
| 4,790,303 A | 12/1988 | Steffee | |
| 4,834,757 A | 5/1989 | Brantigan | |
| 4,878,915 A | 11/1989 | Brantigan | |
| 4,904,260 A | 2/1990 | Ray et al. | |
| 4,904,261 A | 2/1990 | Dove et al. | |
| 4,913,134 A | 4/1990 | Luque | |
| 4,932,975 A | 6/1990 | Main et al. | |
| 4,936,848 A | 6/1990 | Bagby | |
| 4,946,378 A | 8/1990 | Hirayama et al. | |
| 4,961,740 A | 10/1990 | Ray et al. | |
| 4,969,888 A | 11/1990 | Scholten et al. | |
| 5,011,484 A | 4/1991 | Breard | |
| 5,015,247 A | 5/1991 | Michelson | |
| 5,026,373 A | 6/1991 | Ray et al. | |
| 5,035,716 A | 7/1991 | Downey | |
| 5,047,055 A | 9/1991 | Bao et al. | |
| 5,055,104 A | 10/1991 | Ray | |
| 5,059,193 A | 10/1991 | Kuslich | |
| 5,059,194 A | 10/1991 | Michelson | |
| 5,084,049 A | 1/1992 | Asher et al. | |
| 5,092,866 A | 3/1992 | Breard et al. | 606/61 |
| 5,123,926 A | 6/1992 | Pisharodi | |
| 5,167,662 A | 12/1992 | Hayes et al. | |
| 5,180,381 A | 1/1993 | Aust et al. | |
| 5,192,327 A | 3/1993 | Brantigan | |
| 5,258,031 A | 11/1993 | Salib et al. | |
| 5,263,953 A | 11/1993 | Bagby | |
| 5,290,312 A | 3/1994 | Kojimoto et al. | |
| 5,304,178 A | 4/1994 | Stahurski | |
| 5,306,309 A | 4/1994 | Wagner et al. | |
| 5,352,225 A | 10/1994 | Yuan et al. | |
| 5,387,213 A | 2/1995 | Breard et al. | |
| 5,390,683 A | 2/1995 | Pisharodi | |
| 5,395,372 A | 3/1995 | Holt et al. | |
| 5,415,661 A | 5/1995 | Holmes | |
| 5,443,514 A | 8/1995 | Steffee | |
| 5,454,812 A * | 10/1995 | Lin | 606/61 |
| 5,458,638 A | 10/1995 | Kuslich et al. | |
| 5,458,641 A | 10/1995 | Ramirez Jimenez | |
| 5,458,643 A | 10/1995 | Oka et al. | |
| 5,470,333 A | 11/1995 | Ray | |
| 5,496,318 A | 3/1996 | Howland et al. | 606/61 |
| 5,505,732 A | 4/1996 | Michelson | |
| 5,514,180 A | 5/1996 | Heggeness et al. | |
| 5,534,028 A | 7/1996 | Bao et al. | |
| 5,534,029 A | 7/1996 | Shima | |
| 5,540,689 A | 7/1996 | Sanders et al. | |
| 5,549,679 A | 8/1996 | Kuslich | |
| 5,562,736 A | 10/1996 | Ray et al. | |
| 5,593,409 A | 1/1997 | Michelson | |
| 5,609,634 A | 3/1997 | Voydeville | |
| 5,645,597 A | 7/1997 | Krapiva | |
| 5,645,599 A | 7/1997 | Samani | |
| 5,653,761 A | 8/1997 | Pisharodi | |
| 5,662,653 A | 9/1997 | Songer et al. | 606/61 |
| 5,669,910 A | 9/1997 | Korhonen et al. | 606/61 |
| 5,674,295 A | 10/1997 | Ray et al. | |
| 5,674,296 A | 10/1997 | Bryan et al. | |
| 5,676,702 A | 10/1997 | Ratron | |
| 5,702,455 A | 12/1997 | Saggar | |
| 5,725,582 A | 3/1998 | Bevan et al. | |
| 5,766,252 A | 6/1998 | Henry et al. | |
| 5,824,098 A | 10/1998 | Stein | |
| 5,865,846 A | 2/1999 | Bryan et al. | |
| 5,885,299 A | 3/1999 | Winslow et al. | |
| 5,888,224 A | 3/1999 | Beckers et al. | |
| 5,888,226 A | 3/1999 | Rogozinski | |
| 5,976,186 A | 11/1999 | Bao et al. | |
| 5,997,542 A * | 12/1999 | Burke | 606/74 |
| 6,001,130 A | 12/1999 | Bryan et al. | |
| 6,022,376 A | 2/2000 | Assell et al. | |
| 6,113,639 A | 9/2000 | Ray et al. | |
| 6,156,067 A | 12/2000 | Bryan et al. | |
| 6,234,705 B1 | 5/2001 | Troxel | |
| 6,248,106 B1 * | 6/2001 | Ferree | 606/61 |

FOREIGN PATENT DOCUMENTS

| | | |
|---|---|---|
| FR | WO 90/00037 | 1/1990 |
| FR | 2681525 A1 | 3/1993 |
| FR | 2707864 A1 | 1/1995 |
| FR | 2717675 | 9/1995 |
| FR | 2722980 A1 | 2/1996 |
| FR | 2780269 A1 | 12/1999 |
| FR | 2782911 A1 | 3/2000 |
| FR | 2806614 | 9/2001 |
| FR | 2806616 | 9/2001 |
| SU | 1484348 A1 | 6/1989 |
| WO | WO 91/16018 | 10/1991 |
| WO | WO 94/21185 | 9/1994 |
| WO | WO 94/26192 | 11/1994 |
| WO | WO 98/48717 | 11/1998 |
| WO | WO 99/26562 | 6/1999 |
| WO | WO 99/40866 | 8/1999 |
| WO | WO 99/42051 | 8/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 01/28442 A1 | 4/2001 |

* cited by examiner

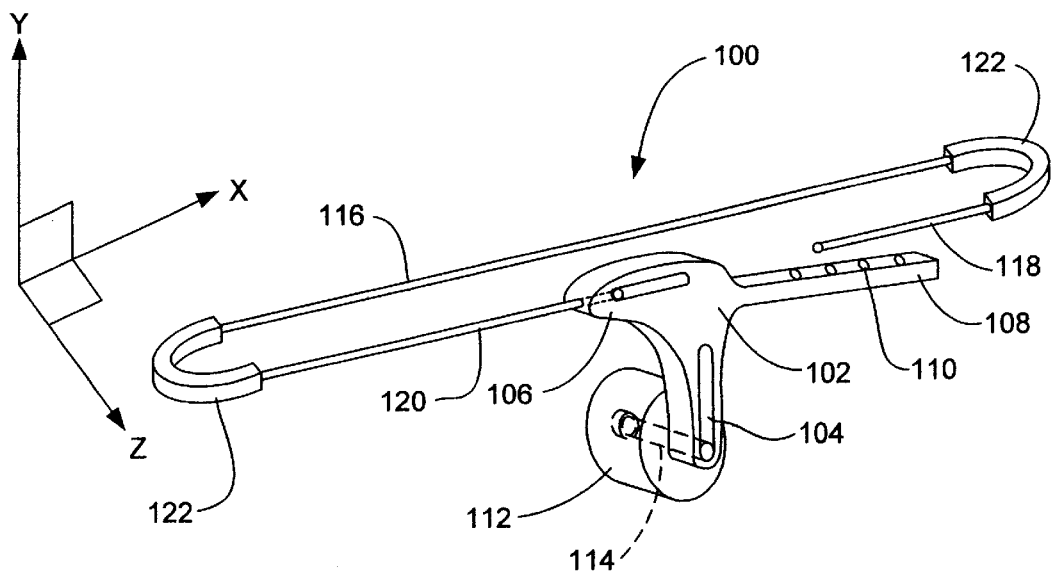
FIG.-1
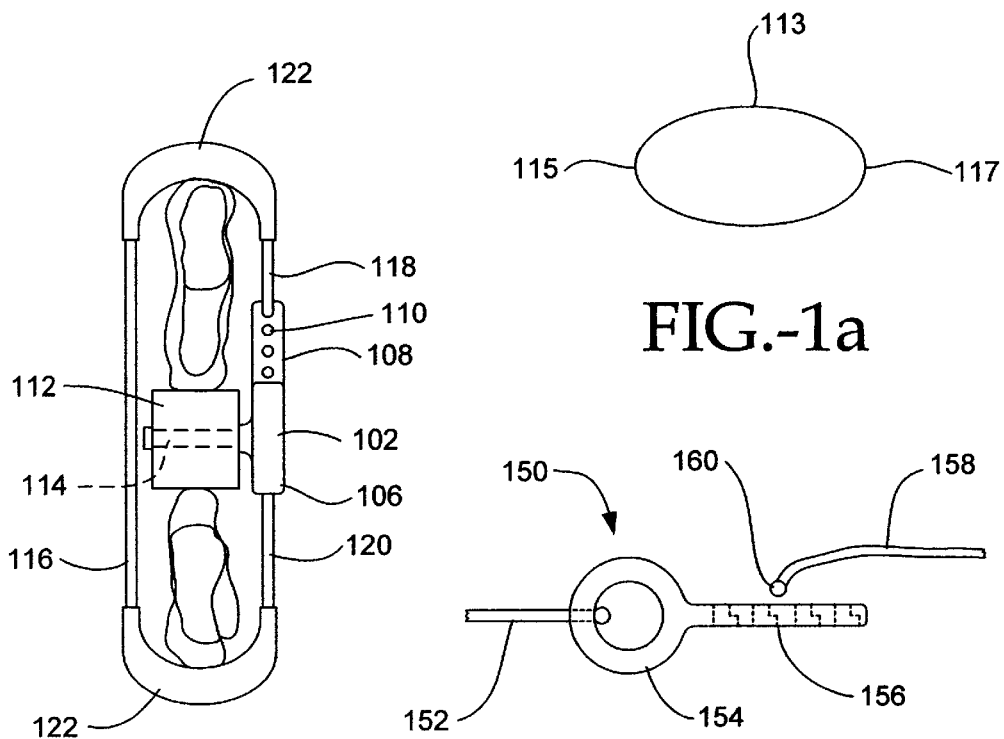
FIG.-1a
FIG.-2    FIG.-3

US 6,582,433 B2

SPINE FIXATION DEVICE AND METHOD

FIELD OF THE INVENTION

The present invention relates to spine fixation devices and methods which supplement a primary spine fusion device, such as by way of example only, an interbody fusion device.

BACKGROUND

A common procedure for handling pain associated with degenerative spinal disk disease is the use of devices for fusing together two or more adjacent vertebral bodies. The procedure is known by a number of terms, one of which is interbody fusion. Interbody fusion can be accomplished through the use of a number of devices and methods known in the art. These include screw arrangements, solid bone implant methodologies, and fusion devices which include a cage or other mechanism which is packed with bone and/or bone growth inducing substances. All of the above are implanted between adjacent vertebral bodies in order to fuse the vertebral bodies together, alleviating associated pain.

It can be advantageous to associate with such primary fusion devices and methods, supplemental devices which assist in the fusion process. These supplemental devices assist during the several month period when bone from the adjacent vertebral bodies is growing together through the primary fusion device in order to fuse the adjacent vertebral bodies. During this period it is advantageous to have the vertebral bodies held immobile with respect to each other so that sufficient bone growth can be established.

Such supplemental devices can include hook and rod arrangements, screw arrangements, and a number of other devices which include straps, wires, and bands, all of which are used to immobilize one portion of the spine relative to another. All of these devices generally require extensive surgical procedures in addition to the extensive procedure surrounding the primary fusion implant.

It would be advantageous if the device and procedure for supplemental spine fixation were as simple and easy to perform as possible, and would optimally leave intact all bone, ligament, and other tissue which comprise and surround the spine. Accordingly, there needs to be developed procedures and implants which are minimally invasive and are supplemental to spine fixation devices and methods.

SUMMARY OF THE INVENTION

One object of the present invention is a device that immobilizes the vertebral bodies by immobilizing the respective spinous process extending therefrom. The device contains a spacer adapted to be positioned between adjacent spinous processes so that the spacer may be located close to the spine. A strap connected with the body is designed to engage the spinous processes, such that the device may be adjusted about the spinous processes. The device ensures that the spacer remains properly positioned between adjacent spinous processes.

Another object of the present invention is a method to insert the device in a manner that minimizes destruction to body tissues. Such a procedure is less traumatic to the patient. Thus, the patient will recover from the procedure faster than with conventional methods.

BRIEF DESCRIPTION OF THE DRAWINGS

FIG. 1 is a perspective view of an embodiment of the present invention, and

FIG. 1*a* is an alternative embodiment of a spacer of the invention;

FIG. 2 is a top view of the embodiment of the present invention of FIG. 1 placed about adjacent spinous processes.

FIG. 3 is a side view of an alternative embodiment of an interlocking mechanism of the embodiment of the present embodiment of FIG. 1.

DETAILED DESCRIPTION OF THE INVENTION

Figure 4:
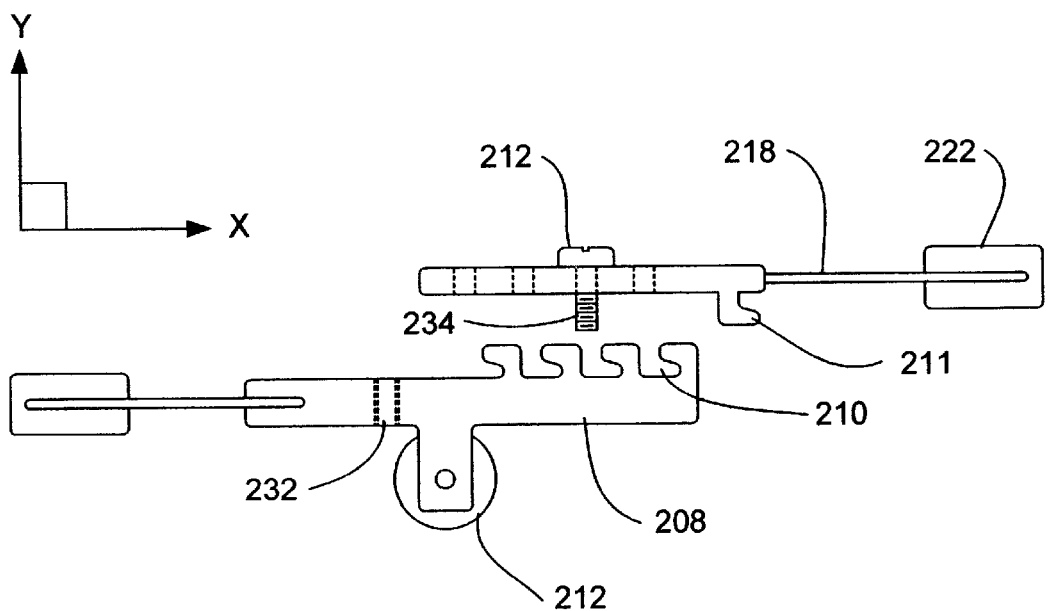
FIG. 4 is a side view of a locking finger assembly of an embodiment of the invention utilized by any of the other embodiments of the present invention.

Referring now to FIG. 1, the device 100 contains a spacer 112, a body 102 and a strap 116. The spacer 112 is substantially cylindrical in shape and is adapted to be positioned close to the spine between adjacent spinous processes to spread the load placed upon the spacer 112 by the adjacent spinous processes (see FIG. 6). However, one of ordinary skill in the art will appreciate that the spacer 112 is not limited to a cylindrical shape. For example, the spacer 112 may be substantially elliptical (FIG. 1*a*) in shape to achieve the same results. The spacer 113 of FIG. 1*a* has narrow ends 115 and 117 which can be placed closer to the spine with the spacer 113 between adjacent spinous processes. The shape of the spacer 112 or 113 is designed so that it conforms to the area that the spacer 112 or 113 is inserted into.

The body 102 contains a first end 104, a second end 106, and a third end 108. The first end 104 supports the spacer 112 so that the spacer 112 is offset from the strap 116, enabling spacer 112 to be closer to the spine than strap 116 in a preferred embodiment. The pin 114 preferably extends from the first end 104 in a substantially perpendicular manner to achieve the offset. Thus, the spacer 112 is offset from the body 102 and from the strap 116. Accordingly, the spacer 112 is positioned close to the spine when the device 100 engages the adjacent spinous processes (see FIG. 6). The spacer 112 can also rotate about the pin 114 so that the spacer 112 can adjust to the contours of the spinous process as the spacer 112 moves closer to the spine. The second end 106 of the body 102 engages the securing end 120 of the strap 116. The third end 108 of the body 102 engages the interlocking end 118 of the strap 116. In FIG. 1, the third end 108 of the body 102 has at least one receiving hole 110 which is capable of accepting the ball-shaped interlocking end 118 of the strap 116. As can be appreciated from reviewing FIG. 5*b*, the ball-shaped interlocking end 118 can be trapped in a receiving hole 110 which has a large opening to receive the interlocking end 118 and a restricted neck or recess for capturing the interlocking end 118. Thus, a secure connection is made when the interlocking end 118 of the strap 116 is inserted into at least one of the receiving holes 110 of the body 102 (see FIG. 2). The spacer 112, body 102 and pin 114 can be made of stainless steel, titanium or other biologically acceptable materials.

In a preferred embodiment of the present invention, the body 102 further has a vertical groove 119 that pin 114 slidably engages. The pin 114 is able to translate along the axis of the vertical groove 119. This allows the spacer 112 to be attached to the body 102, yet still be able to adjust independently.

The strap 116 engages the adjacent spinous processes. The strap 116 can be made of stainless steel or other biologically acceptable materials. Further, the strap 116 may be partly elastic, flexible or elongateable so that a user can secure the interlocking end 118 into the tightest, reachable receiving hole 110, thereby ensuring that strap 116 is secured about the adjacent spinous processes. When the strap 116 is secured to the adjacent spinous processes, the biologically acceptable material 122 contacts the adjacent spinous processes. The biologically acceptable material 122 prevents sharp edges on the strap 116 from digging or cutting into the adjacent spinous processes when strap 116 is secured to the body 102 (see FIG. 2). Such material can include, but is not limited to, silicon. Thus, the strap 116 can be sufficiently tightened about the adjacent spinous processes without damaging them.

There are many different methods whereby the interlocking end 118 of the strap 116 and the third end 108 of the body 102 may be fastened together to form a secure connection between the strap 116 and the body 102. Referring to FIG. 3, the third end 150 of the body 102 contains a strap receiving end 154 and a connector 152. The third end 150 is functionally equivalent to the third end 108 shown in FIG. 1. The connector 152 is attached with the strap receiving end 154 such that the third end 150 of the body 102 is more flexible than the third end 108 shown in FIG. 1. For example, the third end 150 can be made of a flexible biologically compatible material such as, but not limited to, silicon. The strap receiving end 154 has at least one receiving hole 156, thus allowing the strap 158 to firmly engage the adjacent spinous processes. The strap 158 has a ball 160 at the end. By placing strap 158 into receiving hole 156, ball 160 locks strap 158 into place similar to the device in FIG. 1. The purpose of the geometry of the device 150 (FIG. 3) and the device 324 (FIGS. 5a and 5b) is to provide constant tension on the strap 116. These devices, in effect, are elliptical springs which are compressed along the y-axis (see FIG. 5a) to attach the strap.

Figure 4A:
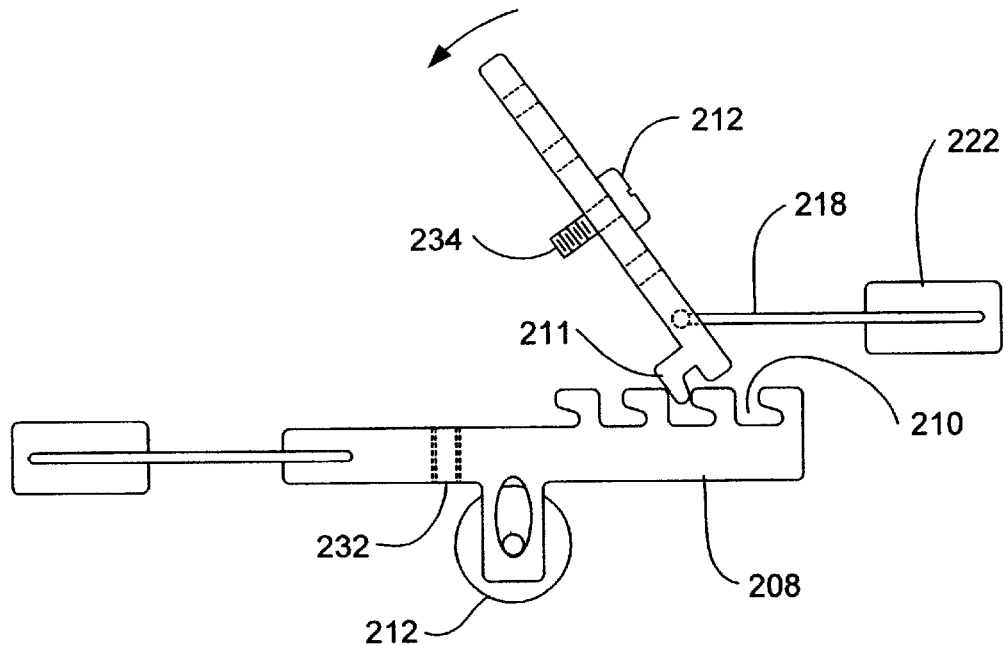

FIG. 4 illustrates yet another embodiment with the strap engaging the third end of the body. The third end 208 of the body 202 has at least one interlocking finger 210 capable of accepting the anchor finger 211 of the interlocking end 218. A secure connection is formed when the anchor finger 211 engages the interlocking finger 210. As the strap 222 may be partly elongateable, the strap 222 may be stretched so that the anchor finger 211 can engage an interlocking finger 210 to ensure that the strap 222 is tightly secured to the adjacent spinous processes. This device functions as a detachable cam lever. For the device to work properly, the attachment of the strap 218 to the lever must be past the anchoring finger 211. The anchoring finger, once engaged, acts as a pivot for the cam lever as shown in FIG. 4a. This is essentially a detachable version of the device in FIG. 8. To provide additional securing, the interlocking end 218 and the third end 208 may be fastened together by a fastening device 212, such as by way of example, a screw. Such a design requires both the interlocking end 218 and the third end 208 to have a hole extending through. Only the third end 208 needs a threaded hole 232. When the interlocking end 218 and the third end 208 are secured by placing the anchoring finger 211 into an interlocking finger 210, the holes 232 and 234 align. Then fastening device 212 can be inserted through holes 232 and 234 to fasten third end 208 and interlocking end 218 together. The hole 232 has threads to engage the fastening device 212.

Figure 5A:
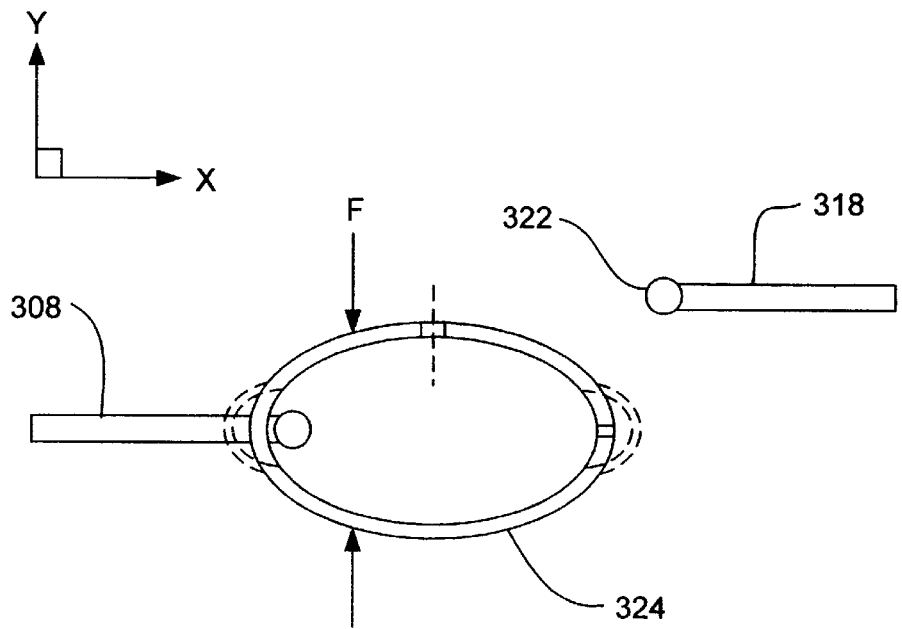
FIG. 5*a* is a side view of a locking ring assembly of an embodiment of the invention utilized by any of the other embodiments of the present invention.
Figure 5B:
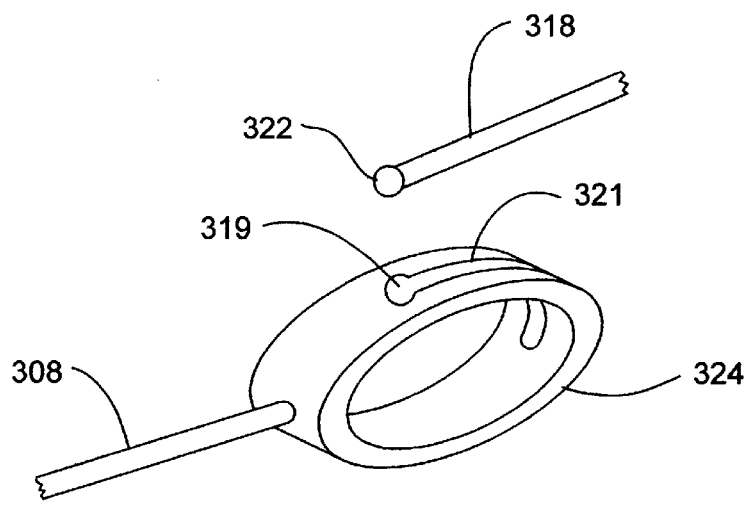
FIG. 5*b* is a perspective view of the locking ring assembly of FIG. 5*a*.

FIGS. 5a and 5b illustrate an additional embodiment with the body and the interlocking end of the strap engaged. The third end 308 of the body may contain an interlocking ring 324. The interlocking ring 324 can be comprised of, but is not limited to, stainless steel or an elastic material such as silicon if an elastic arrangement is desired. The interlocking ring 324 is substantially circular in shape, and as shown by FIG. 5b, has a cut-out 319 similar in shape to the interlocking end 318 of the strap. When the ball 322 on the interlocking end 318 of the strap is inserted into the interlocking ring 324, the interlocking end 318 of the strap cannot easily be removed from the locking ring 324 because the ball 322 is wider than the channel 321 following the cut-out 319 on interlocking ring 324.

The geometry of this device allows it to act as an elliptical spring to provide tension on the strap. Applying compressive force F along the y-axis elongates the elliptical spring along the x-axis allowing connection with the ball end 322. Once the compressive force is released, the spring 324 maintains constant tension on the strap 318.

Figure 8A:
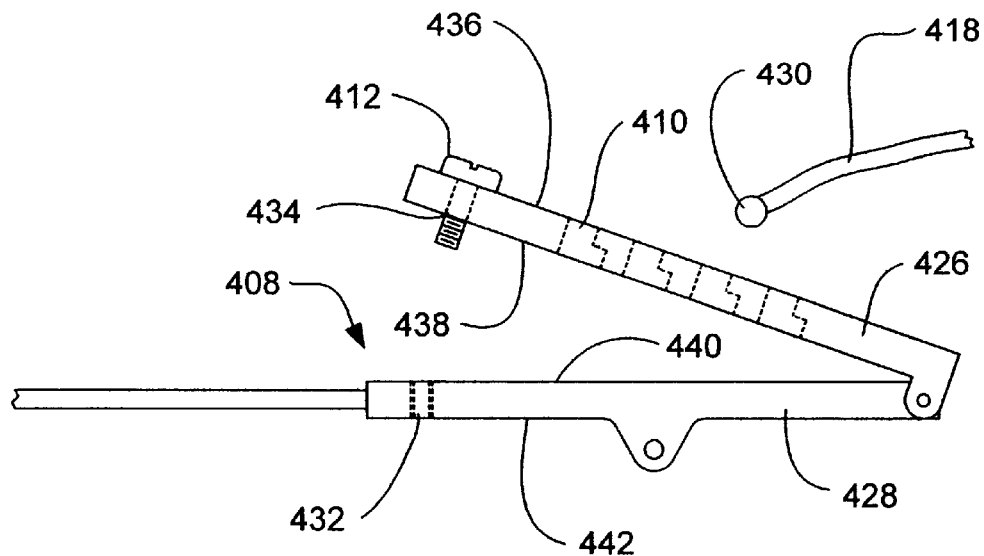
FIG. 8*a* is a side view of a moveable locking assembly of an embodiment of the invention utilized by any of the other embodiments of the present invention.
Figure 8B:
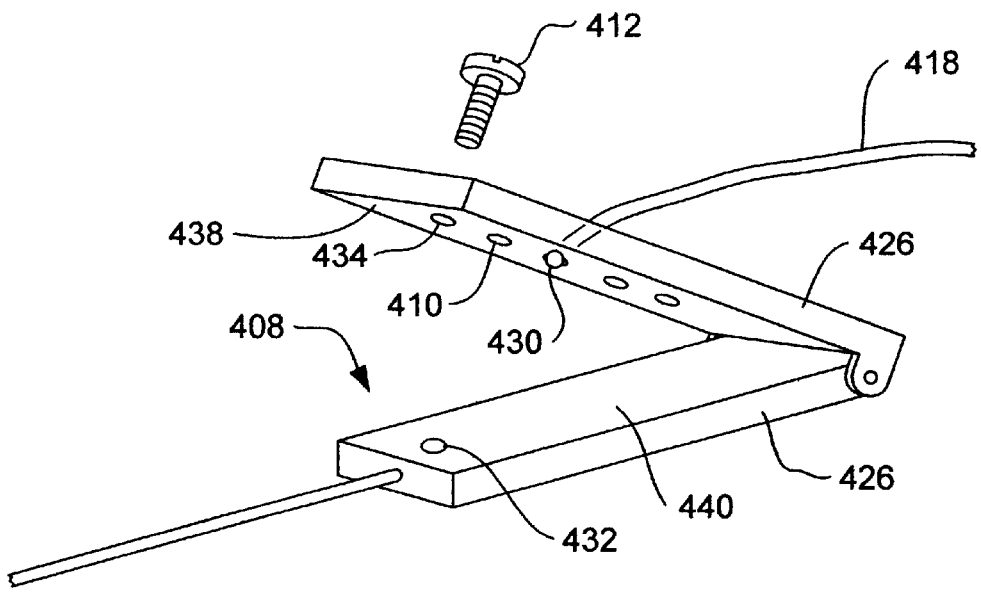
FIG. 8*b* is a perspective view of the collapsible locking assembly of FIG. 8*a*.

FIGS. 8a and 8b illustrate yet another embodiment with the third end of the body and the interlocking end of the strap engaged to secure the strap around the adjacent spinous processes. The third end 408 of the body contains an upper portion 426 and a lower portion 428, coupled at one end. The upper portion 426 has an upper surface 436 and a lower surface 438, and further contains receiving holes 410 and a fastener hole 434. The lower portion 428 has an upper surface 440 and a lower surface 442, and further contains a fastener hole 432. The interlocking end 418 contains a ball 430 at the end of the strap.

To secure the third end 408 to the interlocking end 418, the interlocking end 418 is first placed through one of the receiving holes 410. Receiving hole 410 is designed, as for example seen in FIG. 1 or FIG. 4, so that the ball 430 can be inserted into receiving hole 410, but not removed. Then, the upper portion 426 is pivoted down until the lower surface 438 of the upper portion 426 contacts the upper surface 440 of the lower portion 428. This action tightens strap 116 about the spinous process. As a result, the fastener hole 432 of the lower portion 428 and the fastener hole 434 of the upper portion 426 align. The fastening device 412 can then be placed through the fastener holes 434 and 432. The fastener hole 432 has threads to engage the fastening device 412. Thus, the fastener 412 secures the upper portion 426 and the lower portion 428 together.

Figure 7:
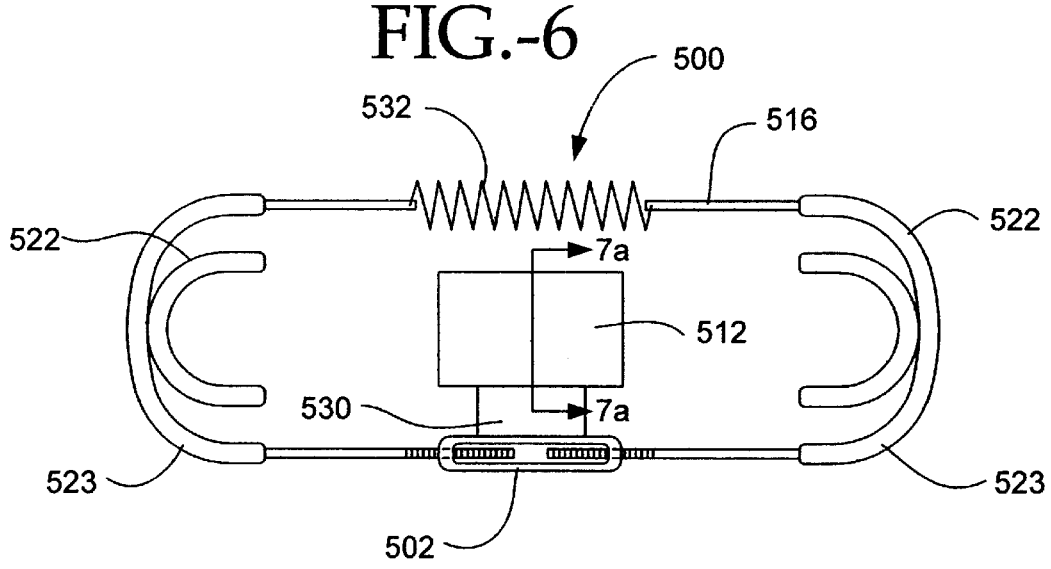
FIG. 7 is a top view of another embodiment of the present invention.
Figure 7A:
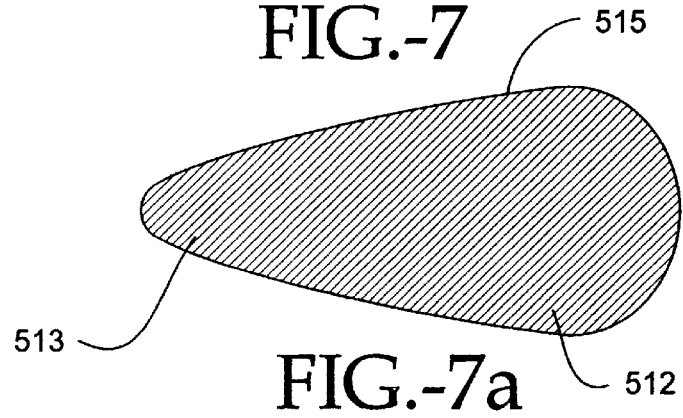
FIG. 7*a* is a cross sectional view through line 7*a*—7*a*.

FIG. 7 illustrates another embodiment of the present invention. The device 500 contains a body 502, a spacer 512 and a strap 516. The spacer 512 may consist of various shapes, such as, but not limited to, an elliptical shape or egg-shaped. One embodiment of the present invention is illustrated in FIG. 7. The egg-shaped spacer 512 has a narrow end 513 and a rounded bulbous end 515 (see FIG. 7a). A portion of strap 516 has a spring element 532. The spring element 532 allows the strap 516 to adjust in length to ensure that the u-shaped end 522 which is connected with biologically acceptable material is in contact with the adjacent spinous processes. The U-shaped end 522 is an inner u-shape which is surrounded by an outer u-shaped end 523 to which the strap 516 is secured. However, the strap needs to be able to slide on the u-shaped end pieces. This allows the spacer to float relative to the adjacent spinous processes. This arrangement illustrates the strap, spring and turnbuckle to be spaced from the spinous process. The spring element 532 also provides constant tension on the strap 516 by constricting the strap 516 around the adjacent spinous processes.

First, the spacer 512 is inserted between the adjacent spinous processes. Then, the strap 516 is placed around the adjacent spinous processes so that the biologically acceptable material 522 contacts the spinous processes, avoiding any sharp edges of the strap 516 from cutting into the spinous processes. The body 502 secures the strap 516 around the adjacent spinous processes. To secure the strap 516 around the adjacent spinous processes, a physician can tighten strap 516 by turning the turnbuckle device of body 502. The spacer 512 is connected with the body 502 by attachment element 530. The attachment element 530 is a flexible biologically acceptable material, such as, but not limited to, silicon. Further, the attachment element 530 offsets the spacer 512 from the body 502 to ensure that spacer 512 is placed near the spine. The combination of the spring element 532 and the body 502 enable a user to tightly secure the device 500 about the adjacent spinous processes. It is to be understood that the spring element 532 can be eliminated from this embodiment if less flexibility is desired.

The present invention is designed to allow a physician to insert the spacer 112 between the adjacent spinous processes while destroying a minimum amount of body tissue. For example, the device 100 can be inserted without modifying the spinous processes or cutting the supra-spinous ligament. Specifically, the device 100 is designed so that the spacer 112 may be inserted between the adjacent spinous processes from one direction. This method is less traumatic for the patient's body, allowing the patient to recover faster.

Figure 6:
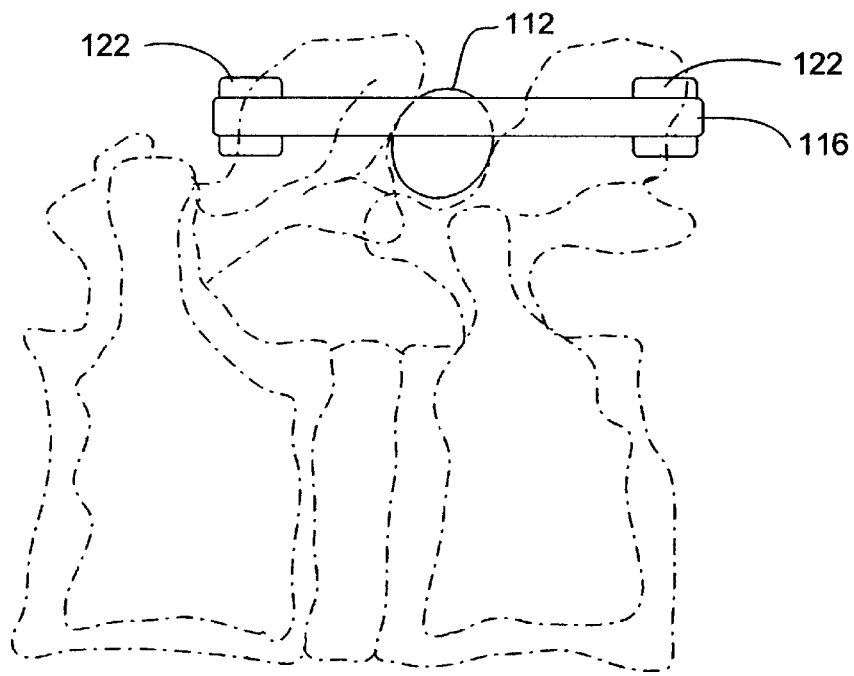
FIG. 6 is a side view of an embodiment of the present invention of FIG. 1 illustrating the position of the spacer and its proximity to the spine.

The method includes several steps. First, the spacer 112 is placed between the adjacent spinous processes so that the spacer 112 is close to the spine. Then, the strap 116 is placed around the adjacent spinous processes such that the biologically acceptable material 122 is in contact with both spinous processes. Last, the interlocking end 118 of the strap 116 is secured to the third end 108 of the body 102. The various methods for securing the interlocking end 118 of the strap 116 to the third end 108 of the body 102 is as previously described. The device 100 as installed is shown in FIG. 2 and FIG. 6.

The foregoing description of preferred embodiments of the present invention has been provided for the purposes of illustration and description. It is not intended to be exhaustive or to limit the invention to the precise forms disclosed. Many modifications and variations will be apparent to practitioners skilled in the art. The embodiments were chosen and described in order to best explain the principles of the invention and its practical application, thereby enabling others skilled in the art to understand the invention with various embodiments and with various modifications as are suited to the particular use contemplated. It is intended that the scope of the invention be defined by the following claims and their equivalents.

What is claimed is:

1. A device that immobilizes vertebral bodies by immobilizing respective spinous processes extending therefrom, comprising:
    a spacer adapted to be positioned between adjacent spinous processes;
    a body connected with the spacer such that the position of the spacer can be adjusted relative to the body; and
    a strap connected with the body and adapted to engage the adjacent spinous processes.

2. The device according to claim 1, whereby the spacer is substantially elliptical in shape.

3. The device according to claim 2, whereby the spacer is adapted to be positioned close to the spine and adjacent to portions of the spinous processes to spread the load placed upon the spacer by the adjacent spinous processes.

4. The device according to claim 1, whereby the spacer is substantially cylindrical in shape.

5. The device according to claim 4, whereby the spacer is adapted to be positioned close to the spine and adjacent to portions of the spinous processes to spread the load placed upon the spacer by the adjacent spinous processes.

6. The device according to claim 1, whereby the strap has a securing end and an interlocking end that attach with the body.

7. The device according to claim 6, whereby the spacer is connected with a first end of the body, and whereby the body has a second end for engaging the securing end of the strap, and a third end for engaging the interlocking end of the strap.

8. The device according to claim 7, whereby the third end of the body has at least one receiving hole capable of accepting the interlocking end of the strap and forming a secure connection when the interlocking end of the strap is inserted into the receiving hole.

9. The device according to claim 7, whereby the third end of the body has at least one interlocking finger capable of accepting the interlocking end of the strap and forming a secure connection when the interlocking end of the strap is attached with the interlocking finger.

10. The device according to claim 9, whereby the third end of the body and the interlocking end of the strap also have a hole extending therethrough so that when the interlocking end of the strap and the third end of the body are secured, the holes align allowing for a fastening device to be inserted, thus providing additional securing.

11. The device according to claim 7, whereby the third end of the body contains a locking ring assembly capable of accepting the interlocking end of the strap and forming a secure connection when the interlocking end of the strap is inserted into the locking ring assembly.

12. The device according to claim 7, whereby the third end of the body contains a moveable locking device capable of accepting the interlocking end of the strap and forming a secure connection when the interlocking end of the strap is inserted into the moveable locking device.

13. The device according to claim 1, whereby the body has a first end that supports a pin extending substantially perpendicular from the first end of the body so that the pin can support the spacer in relation to the body.

14. The device according to claim 13, whereby the spacer is movably attached to the body so that the spacer can adjust to the contours of the spinous processes as the spacer moves closer to the spine.

15. The device according to claim 1, whereby the strap has biologically acceptable material placed on a portion thereof so that the material contacts the spinous process when the strap is secured to the spinous process, thus preventing any sharp edges of the strap from cutting into the spinous process.

16. The device according to claim 1, whereby the spacer is adapted to be located close to the spine.

17. The device according to claim 1, whereby the device may be adjusted so that the strap is positioned about the adjacent spinous processes, ensuring that the spacer remains positioned between adjacent spinous processes.

18. The device according to claim 1, whereby the strap maintains constant tension on the spinous process.

19. A method for rigidly positioning adjacent spinous processes, including the steps, in any order, of:

placing a spacer connected with a body between adjacent spinous processes by inserting the spacer between the spinous processes;

adjusting the position of the spacer relative to the body;

positioning a strap connected with the body around adjacent spinous processes; and securing the strap to the body.

20. The method according to claim 19, whereby an interlocking end of the strap engages at least one receiving member of the body, and the additional step of causing the interlocking end of the strap and the receiving member of the body to interlock together so that the strap is fastened to adjacent spinous processes.

21. The method of claim 20, whereby securing the strap to the body includes fastening the interlocking end of the strap with the receiving member of the body by placing an interlocking finger of the interlocking end of the strap into the receiving member of the body so that the strap is held in place.

22. The method of claim 21, whereby securing the strap to the body further includes placing a fastener through holes that align between the interlocking end of the strap and the receiving member of the body.

23. The method of claim 20, whereby securing the strap to the body includes engaging the interlocking end of the strap with a receiving member of the body by placing a ball at the end of the interlocking end of the strap into a ring assembly of the body so that the strap is held in place.

24. The method of claim 20, whereby securing the strap to the body includes engaging the interlocking end of the strap with a receiving member of the body by placing the ball at the end of the interlocking end of the strap into a moveable locking device of the body, and by further fastening a fastening device through the moveable locking device.

25. The method according to claim 19, whereby the spacer placed between adjacent spinous processes is elliptical in shape with a narrow end, wherein the step of placing the spacer between adjacent spinous processes includes positioning the narrower end of the spacer closer to the spine.

26. The method according to claim 19, including the step of positioning the strap around the adjacent spinous processes such that a biologically acceptable material covering a portion of the strap is in contact with the adjacent spinous processes, thus avoiding any sharp edges of the strap from contacting the adjacent spinous processes.

27. The method according to claim 26, whereby the step of positioning the strap around the adjacent spinous processes does not require altering the adjacent spinous processes to secure the strap around the adjacent spinous processes.

28. A method for rigidly positioning adjacent spinous processes, including the steps, in any order, of:

placing a spacer by a body between adjacent spinous processes by inserting the spacer between the spinous processes positioning a strap secured to the body around adjacent spinous processes;

securing the strap to the body; and whereby an interlocking end of the strap engages at least one receiving member of the body, and the additional step of causing the interlocking end of the strap and the receiving member of the body to interlock together so that the strap is fastened to adjacent spinous processes; and whereby securing the strap to the body includes engaging the interlocking end of the strap with a receiving member of the body by placing a ball at the end of the interlocking end of the strap into at least one of a plurality of receiving holes of the body so that the strap is held in place.

29. A method for rigidly positioning adjacent spinous processes, including the steps, in any order, of:

placing a spacer supported by a body between adjacent spinous processes by inserting the spacer between the spinous processes from one side of the spinous processes, thus injuring less body material and allowing the patient to recover faster;

adjusting the position of the spacer relative to the body;

positioning a strap connected with the body around adjacent spinous processes; and securing the strap to the body.

30. The method according to claim 29, whereby an interlocking end of the strap engages at least one receiving member of the body, and the additional step of causing the interlocking end of the strap and the receiving member of the body to interlock together so that the strap is fastened to the adjacent spinous processes.

31. The method according to claim 29, whereby the spacer placed between two adjacent spinous processes is elliptical in shape with a narrow end, wherein placing the spacer includes positioning the narrower end of the spacer closer to the spine.

32. The method according to claim 29, including positioning the strap around the adjacent spinous processes such that a biologically acceptable material covering a portion of the strap is in contact with the adjacent spinous processes prevents any edges of the strap from contacting the adjacent spinous processes.

33. The method according to claim 29, whereby the step of positioning the strap around the adjacent spinous processes does not require altering the adjacent spinous processes to secure the strap around the adjacent spinous processes.

34. The method of claim 29, whereby the securing step includes securing the strap to the body by engaging an interlocking end of the strap with a receiving member of the body by placing an interlocking finger of the interlocking end of the strap into at least one of the interlocking fingers of the body so that the strap is held in place.

35. The method of claim 34, whereby the securing step further includes placing a fastener through holes that align between the interlocking member of the strap and the receiving member of the body.

36. The method of claim 29, whereby the securing step includes fastening the strap to the body by engaging the interlocking end of the strap with the receiving member of the body by placing a ball at the end of an interlocking end interlocking end of the strap into a ring assembly of the body so that the strap is held in place.

37. The method of claim 29, whereby the securing step includes fastening the strap to the body by engaging the interlocking end of the strap with the receiving member of the body by placing a ball at the end of the interlocking end of the strap into a moveable locking device of the body, and by further fastening a fastening device through the moveable locking device.

38. A method for rigidly positioning adjacent spinous processes, including the steps, in any order, of:

placing a spacer supported by a body between adjacent spinous processes by inserting the spacer between the spinous processes from one side of the spinous processes, thus injuring less body material and allowing the patient to recover faster;

positioning a strap secured to the body around adjacent spinous processes;

securing the strap to the body; and whereby the securing step includes securing the strap to the body by engaging an interlocking end of the strap with a receiving member of the body by placing a ball at the end of the interlocking end of the strap into at least one of a plurality of receiving holes of the body so that the strap is held in place.

39. A device that immobilizes vertebral bodies by immobilizing respective spinous processes extending therefrom, comprising:

a spacer that is adapted to be placed between the spinous processes;

a strap that is adapted to be placed about the spinous processes; and a body that couples the spacer to the strap with the spacer offset from the strap along a sagittal plane so that the spacer can be placed closer to a spine than the strap.

40. The device according to claim 39, wherein the spacer is cylindrical in shape.

41. The device according to claim 39, wherein the spacer is elliptical in shape.

42. The device according to claim 39, wherein the spacer is egg-shaped in shape.

43. The device according to claim 39, wherein the strap is at least in part flexible.

44. The device according to claim 39, wherein the strap is at least in part elastic.

45. The device according to claim 39, wherein the strap is at least in part elongateable.

46. A device that immobilizes vertebral bodies by immobilizing respective spinous processes extending therefrom, comprising:

a spacer that is adapted to be placed between the spinous processes;

a strap that is adapted to be placed about the spinous processes;

a body that couples the spacer to the strap with the spacer offset from the strap so that the spacer can be placed closer to a spine than the strap; and wherein the spacer is rotatably mounted to the body.

47. A device that immobilizes vertebral bodies by immobilizing respective spinous processes extending therefrom, comprising:

a spacer that is adapted to be placed between the spinous processes;

a strap that is adapted to be placed about the spinous processes;

a body that couples the spacer to the strap with the spacer offset from the strap so that the spacer can be placed closer to a spine than the strap; and wherein the body includes a member extending therefrom, with the spacer rotatably mounted to the member.

48. The device according to claim 47, wherein the strap defines a plane and the member is spaced from the plane and is parallel to the plane.

49. A device that immobilizes vertebral bodies by immobilizing respective spinous processes extending therefrom, comprising:

a spacer that is adapted to be placed between the spinous processes;

a strap that is adapted to be placed about the spinous processes;

a body that couples the spacer to the strap with the spacer offset from the strap so that the spacer can be placed closer to a spine than the strap; and wherein the strap has a fastener that tightens the strap.

50. A device that immobilizes vertebral bodies by immobilizing respective spinous processes extending therefrom, comprising:

a spacer that is adapted to be placed between the spinous processes;

a strap that is adapted to be placed about the spinous processes;

a body that couples the spacer to the strap; and wherein the spacer is rotatably mounted to the body.

51. A device that immobilizes vertebral bodies by immobilizing respective spinous processes extending therefrom, comprising:

a spacer that is adapted to be placed between the spinous processes;

a strap that is adapted to be placed about the spinous processes, said strap defining a plane;

a body that couples the spacer to the strap; and wherein the body includes a member extending therefrom, with the spacer rotatably mounted to the member.

52. A device that immobilizes vertebral bodies by immobilizing respective spinous processes extending therefrom, comprising:

a spacer that is adapted to be placed between the spinous processes;

a strap that is adapted to be placed about the spinous processes, said strap defining a plane;

a body that couples the spacer to the strap with the spacer offset from the strap so that the spacer can be placed closer to a spine than the strap; and wherein the spacer has an axis that is parallel to the plane defined by the strap.

* * * * *

UNITED STATES PATENT AND TRADEMARK OFFICE
CERTIFICATE OF CORRECTION

PATENT NO.    : 6,582,433 B2
DATED         : June 24, 2003
INVENTOR(S)   : David Yun It is certified that error appears in the above-identified patent and that said Letters Patent is hereby corrected as shown below:

Column 7,
Line 58, after "processes", please add -- ; --.

Column 8,
Line 49, please delete "member" and insert therefor, -- end --.
Line 55, please delete "interlocking end".

Signed and Sealed this

Seventh Day of October, 2003

JAMES E. ROGAN
*Director of the United States Patent and Trademark Office*